United States Patent

Razaq

Patent Number: 5,322,602
Date of Patent: Jun. 21, 1994

[54] GAS SENSORS

[75] Inventor: Mohammed Razaq, Hacienda Heights, Calif.

[73] Assignee: Teledyne Industries, Inc., Los Angeles, Calif.

[21] Appl. No.: 10,626

[22] Filed: Jan. 28, 1993

[51] Int. Cl.⁵ ............................................. G01N 27/26
[52] U.S. Cl. ........................... 204/153.22; 204/153.18; 204/424; 204/421; 204/431; 204/432; 204/415; 204/418
[58] Field of Search ....................... 204/153.18, 153.22, 204/418, 424, 421, 431, 432, 412, 430, 153.1, 415; 429/33; 521/27, 28; 422/88

[56] References Cited

U.S. PATENT DOCUMENTS

| | | | |
|---|---|---|---|
| 3,776,832 | 12/1973 | Oswin et al. | 204/195 R |
| 4,514,278 | 4/1985 | Stephens et al. | 204/430 |
| 4,900,405 | 2/1990 | Otagawa et al. | 204/1 T |
| 4,954,238 | 9/1990 | Kato et al. | 204/430 |
| 5,085,760 | 2/1992 | Razaq et al. | 204/431 |
| 5,132,193 | 7/1992 | Reddey et al. | 429/13 |
| 5,164,053 | 11/1992 | Razaq et al. | 204/153.18 |

OTHER PUBLICATIONS

F. A. Keidel, Analytical Chemistry, vol. 31, No. 12, p. 2043 (1959).
Huang, Analytical Chemistry, vol. 63, No. 15, Aug. 1, 1991, pp. 1570–1573.

Primary Examiner—John Niebling
Assistant Examiner—Bruce F. Bell
Attorney, Agent, or Firm—Edward J. DaRin

[57] ABSTRACT

An improved perfluorinated, ion-exchange polymer, either in the form of a membrane or a thin film useful as the electrolyte in chemical sensors. The polymer is treated with an acid, such as boric acid or a mixture of boric acid and phosphoric acid, to maintain the ionic conductivity of the polymer to approximately 180 degrees Centigrade. The improved polymer electrolyte is utilized to sense moisture by a two electrode structure with the electrodes arranged in interdigital fashion and the electrolyte film cast over the electrodes. The electrolyte is included in a 3 electrode sensor for sensing various types of gases.

28 Claims, 7 Drawing Sheets

ELECTROLYTE ELEMENT- EL

SOLID, PERFLUORINATED, ION-EXCHANGE POLYMER TREATED WITH BORIC ACID OR PRESELECTED MIXTURE OF BORIC AND PHOSPHORIC ACID FOR MAINTAINING IONIC CONDUCTIVITY TO TEMPERATURES UP TO 180 DEGRESS CENTIGRADE

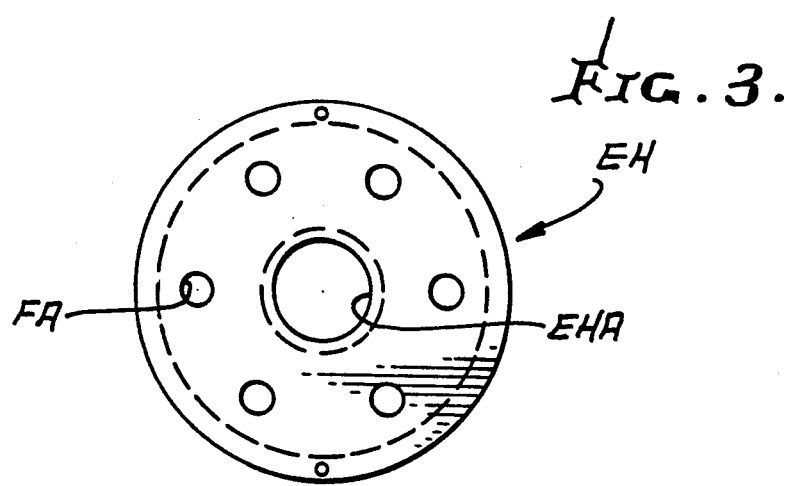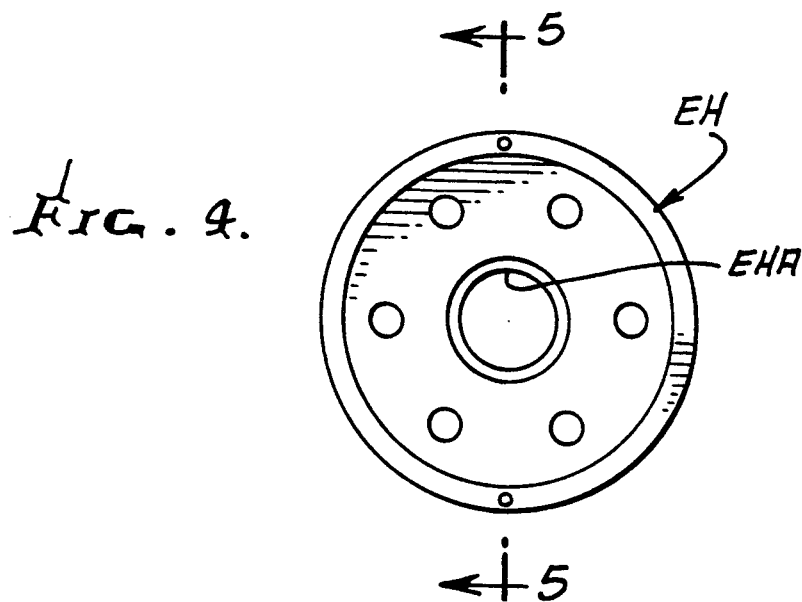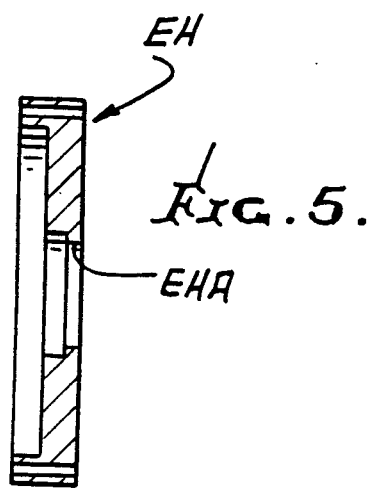

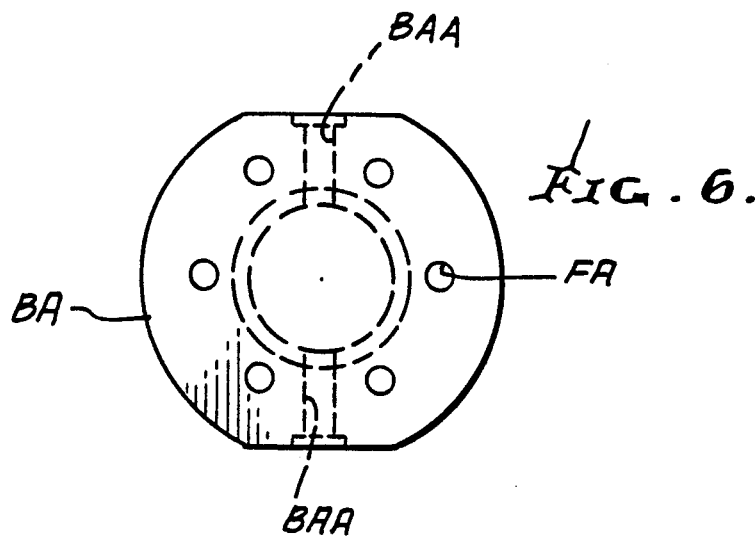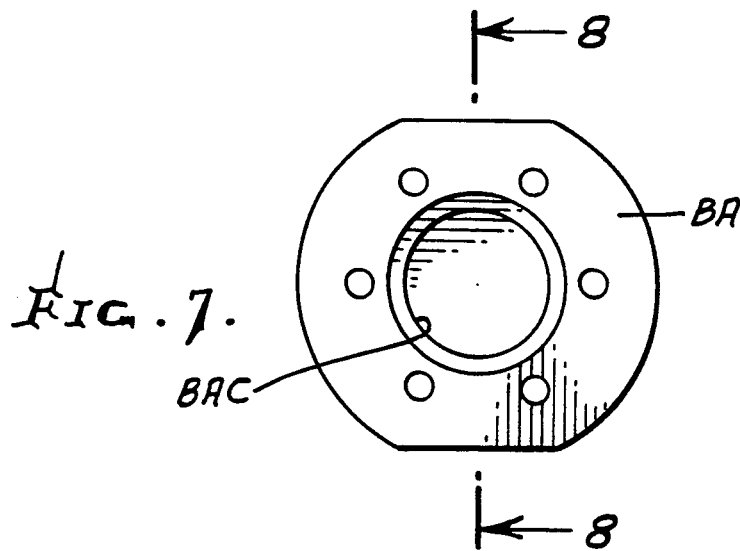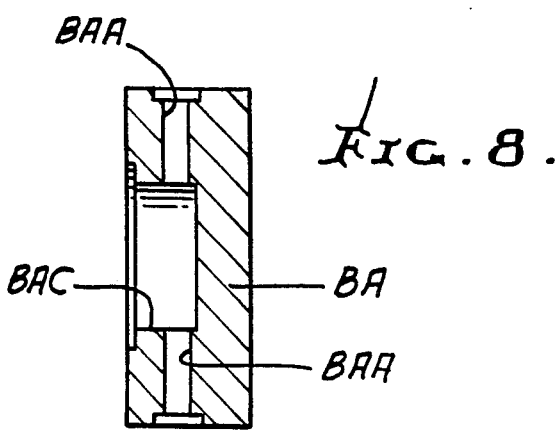

GAS SENSORS

FIELD OF INVENTION

This invention relates to gas sensors and more particularly to improvements in solid, perfluorinated ion-exchange polymers useful as electrolytes in chemical sensors and the improved sensors constructed with the improved electrolyte element in both the two electrodes, galvanic, configurations and the three electrode, polarographic, structures.

CROSS-REFERENCE

This invention is an improvement of the treated, solid ion-exchange polymer electrolyte element and the electrochemical sensing cell disclosed and claimed in the application bearing Ser. No. 513,091, filed on Apr. 23, 1990, now U.S. Pat. No. 5,164,053 granted on Nov. 17, 1992, and assigned to the same assignee as the present application. In this prior disclosure, the electrochemical sensing cell is limited to sensing only a few gases, namely oxygen and hydrogen. As to the electrodes useful on an electrochemical sensor capable of sensing reactive gases in the parts per billion range, the electrodes disclosed and claimed in U.S. Pat. No. 5,085,760 granted on Feb. 4, 1992 and owned by the same assignee as the present invention, are useful in the present invention, as well, for electrochemical sensing of gases.

BACKGROUND OF INVENTION

The efficiency of semiconductor and integrated circuit fabrication process is sensitive to not only the quality of the materials utilized in the fabrication procedure but also the environment of the fabrication location. In the prior U.S. Pat. No. 5,085,760, the invention was directed to sensing or monitoring the very low levels of oxygen, in the parts per billion range, present in the inert blanketing gases required in the fabrication procedures. A similar problem in the fabrication process is that the presence of very low levels of moisture in the gas feed stream can severely effect both the yield and the quality of the integrated circuits or the like. In the past, a variety of sophisticated analytical instruments to monitor the moisture in a gas feed stream from high parts per million (ppm) to sub-parts per billion (ppb) levels were developed. Many of these prior art instruments utilized for sub-parts per billion (ppb) level measurements are relatively complex and expensive. The prior art instruments based on the electrolytic mechanism for decomposing or splitting the water in gases are relatively simple and inexpensive but lack the sensitivity to measure moisture in sub parts per billion levels and exhibit the sluggish response and recovery time. These electrolytic hygrometers utilized the principles disclosed by F. A. Keidel in Analytical Chemistry, Vol. 12, page 2043(1959). This well known, prior art hygrometer consists of an electrolytic cell having a pair of electrodes covered with a hygroscopic electrolyte such as Phosphorous Pentoxide $P_2O_5$. In this sensor, the water vapors in the gas are absorbed at the surface of the hygroscopic layer and electrolyzed to gaseous oxygen and hydrogen. The current drawn by the electrolytic cell is a direct measure of the water being electrolyzed. At equilibrium, the cell current and the gas flow rate gives the absolute and continuous measurement of the amount of water in the gas stream.

Electrolytic cells with the different physical configurations based on the Keidel principles have been disclosed in the literature. The most noticeable and frequently used physical configuration is in the form of a tubular conduit having a pair of electrode wires helically positioned in parallel on the inner wall of the conduit from end to end or alternatively an interdigitated grid of electrodes deposited on an insulating surface that is coated with a thin layer of a hygroscopic film, $P_2O_5$, derived from the dehydration of a thin layer of phosphoric acid by electrolysis at elevated temperatures. The major problems experienced with such a configuration is that the electrolytic layer(1) upon prolonged exposure to high moisture levels, is converted to phosphoric acid that tends to run off the electrodes and (2) upon the prolonged exposure to gases with moisture levels in the sub parts per billion level causes the electrolytic layer to crack. Both of these undesirable conditions cause discontinuity in the electrolyte layer and as a result the sensor loses its sensitivity. In addition, when the electrolyte layer is fully dehydrated, the sensor's response to small changes in the moisture content becomes very sluggish.

A solid, perfluorinated, ion-exchange polymer of the prior art, commercially available from E.I. du Pont de Nemours & Company, Inc. of Wilmington, Del. and commercially identified as a "Nafion" element, has been used as the electrolyte element in an electrolytic sensor. This ion-exchange polymer in the form of a thin film sandwiched between a pair of electrodes for trace water sensing and is disclosed in the U.S. Pat. No. 4,514,278 granted on Apr. 30, 1985. U.S. Pat. No. 4,954,238 granted on Sep. 4, 1990, discloses a moisture sensing hygrometer element in the form of an ion-exchange film of the "Nafion" type cast on the pair of electrodes on a tubular substrate. These "Nafion" devices are considered to have less disadvantages than those inherent in the Keidel-phosphorous pentoxide films. However, these "Nafion" based humidity sensors are less sensitive by more than two orders of magnitude compared to those using $P_2O_5$ with identical physical configurations and with a proportionate effect on the lower detection limit. The lower sensitivity with perfluorinated ion-exchange polymer electrolyte ("Nafion") is primarily due to the decreased ionic conductivity of the "Nafion" polymer in the presence of lower levels of moisture. It is well known that water is essential for solvating the hydrogen ions of the sulfonic acid groups of the "Nafion" polymer for the ionic conduction to occur in the "Nafion" membrane. This is considered to preclude the use of the ion-exchange polymer as the electrolyte element in either very dry environments or at temperatures above 100 degrees Centigrade with unhumidified gases and without the means to supply water to the polymer.

In the above referenced prior U.S. Pat. No. 5,164,053, an improved electrochemical sensing cell is disclosed that utilizes a solid, perfluorinated ion-exchange polymer (PFIEP) element as an electrolyte element in the sensor. The electrolyte element taught to the art by the aforementioned patent utilizes a solid polymer electrolyte that has been equilibrated with phosphoric acid for maintaining the ionic conductivity of the polymer up to temperatures on the order of 180 degrees Centigrade. This prior patent teaches the solvation of the hydrogen ions of the sulfonic acid groups of the ion-exchange by the phosphoric acid that provides with a hydrogen bonding network for maintaining the ionic conductivity of the polymer without the need to add water to the polymer. This general structure is represented as follows:

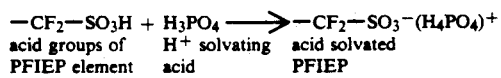
acid groups of PFIEP element + H+ solvating acid → acid solvated PFIEP It has only recently become known that it has been reported in the literature that incorporating phosphoric acid in a solution of the "Nafion" material for an electrolytic moisture sensor has been found to function in relatively dry environments with better sensitivity than the known prior art. This is disclosed by Huang et al. in Analytical Chemistry, Vol. 63, No. 15 for Aug. 1, 1991 on pages 1570–1573. The known humidity sensors for detecting sub parts per million moisture levels are typically powered at 30–100 volts. Under such electrical operating conditions phosphoric acid is readily converted into the dehydrated form of phosphorous pentoxide, $P_2O_5$. This causes the electrolyte layer to lose its continuity and thereby the sensor loses its sensitivity. I have found that in a phosphoric acid, equilibrated perfluorinated ion-exchange polymer electrolyte used for electrochemical sensors, where the voltage between two electrodes is typically less than 1.23 volts (1.23 volts is the thermodynic voltage between the hydrogen and oxygen electrodes), as disclosed in U.S. Pat. No. 5,164,053, that the phosphoric acid is not converted to the dehydrated form and thus the conductivity of the electrolyte element is maintained. I have also determined that a moisture sensor utilizing a phosphoric acid treated, solid, perfluorinated ion-exchange polymer electrolyte element where the voltage is typically between 30–100 volts, over a prolonged period of time and in a very dry environment, (moisture levels in the lower end of the parts per billion levels), phosphoric acid is partially converted to the $P_2O_5$ form and thereby results in decreasing the sensitivity of the sensor.

A further aspect of the prior art is found in the U.S. Pat. No. 4,900,405 granted on Feb. 13, 1990 for a "Surface Type Microelectronic Gas and Vapor Sensor". This prior art principally discloses various micro-sensing structures having two, three or more electrode structures deposited in close proximity to one another on the same side of an active area on a surface of the substrate so that the ion migration is fast. The substrates may be constructed of an electrically insulative material or of a semiconductor material. These structures utilize solid, electrolytes including ion-exchange polymers of the "Nafion" type and takes advantage of the hydrophobic nature of such a polymer. All of the disclosed structures, however, utilizing the "Nafion" type ion-exchange member require the use of an aqueous reservoir in contact with the solid electrolyte medium to keep it from drying out and inactivating the disclosed microsensor. This problem is solved by the disclosure in the aforementioned U.S. Pat. No. 5,164,053 and further improved upon herein.

Another piece of prior art, utilizing an aqueous electrolyte with 3 electrodes, discloses a means to enable the various impurities in the environmental air to be distinctly detected and measured is found in U.S. Pat. No. 3,776,832. The gases, noxious atmospheric pollutants were selected from the group consisting of carbon monoxide, nitric oxide, hydrocarbons, ethanol and methanol in air. This is accomplished by conveying the same air sample through a series of individual cells, with each cell being constructed and defined to detect only a single impurity. This prior art patent discloses the use of potentiostat circuit means for maintaining a constant or fixed relative potential difference between the anode or sensing electrode and the reference electrode of the 3 electrode sensors with the voltage selected in accordance with the gas species to be sensed.

There is, then, a present need for an improved, relatively inexpensive electrochemical/electrolytic sensor with a greater stability and faster responses and recovery times than those presently known and in commercial use that are not subject to drying out during continuous use.

SUMMARY OF INVENTION

The present invention provides an improved, inexpensive, solid electrolyte element that is constructed of a solid, perfluorinated, ion-exchange polymer ("Nafion") that has been treated with phosphoric acid or boric acid or a preselected mixture of boric acid and phosphoric acid as the electrolyte element of a sensor that maintains its ionic conductivity over extended periods of time. The aforementioned types of acid equilibrated, solid, perfluorinated, ion-exchange polymers can be used as the electrolyte element in any electrolytic cell for detecting any electro-active species of gas where the reactants or the products thereof do not chemically react with the aforementioned ion-exchange polymer so that the ionic conductivity of the polymer is lost.

As to the sensing cells incorporating the improved electrolytic element, an electrolytic sensor is produced by the attachment of a preselected number of electrodes of suitable conductive material to achieve the electrolytic action in the form of a galvanic or polarographic type. An electrochemical sensor employing the improved electrolyte element can be produced by sandwiching the improved electrolyte element between a pair of gas permeable or gas diffusion electrodes in a galvanic cell configuration as disclosed in the aforementioned U.S. Pat. No. 5,164,053, or by applying two or three electrodes on the same side of the improved electrolyte element in a polarographic type. The improved electrolyte may also be utilized in an electrochemical sensor of either two or three electrodes for sensing certain electroactive gas species.

From a broad, structural standpoint, the improved electrolytic element may be in the form of a thin membrane or a thin film of a perfluorinated, ion-exchange polymer element treated with an acid for maintaining the ionic conductivity thereof to temperatures up to a 180 degrees Centigrade. The acid treatment of the polymer is with boric acid alone or a preselected mixture of boric and phosphoric acids.

From a sensor standpoint, an electrolytic sensor may be produced by the deposition of a thin film of the treated ion-exchange polymer over a substrate mounting a plurality of electrodes for sensing the moisture in a gas or a specific gas species, when a 3 electrode structure is utilized. The same treated electrolyte element in the form of a membrane may be used as an electrochemical sensor for sensing selected gases in either a two or three electrode configuration. In the three electrode configuration, potentiostat circuit means are utilized to maintain a fixed, potential between the sensing electrode and the reference electrode in accordance with the species of gas desired to be sensed.

BRIEF DESCRIPTION OF THE DRAWINGS

These and other features of the present invention may be more fully appreciated when considered in light of the following specification and drawings, in which:

FIG. 3 is a detached, front elevational view of the sensor holder of FIG. 2;

FIG. 4 is a detached, rear elevational view of the sensor holder of FIG. 3;

FIG. 5 is a cross-sectional view, taken along the line 5—5 of FIG. 4;

FIG. 6 is a detached, bottom elevational view of the sensor block of FIG. 2, with portions in dotted outline;

FIG. 7 is a detached, top elevational view of the sensor block of FIG. 6;

FIG. 8 is a cross-sectional view, taken along the line 8—8 of FIG. 7;

DETAILED DESCRIPTION OF THE PREFERRED EMBODIMENTS

Figures 1, 15:
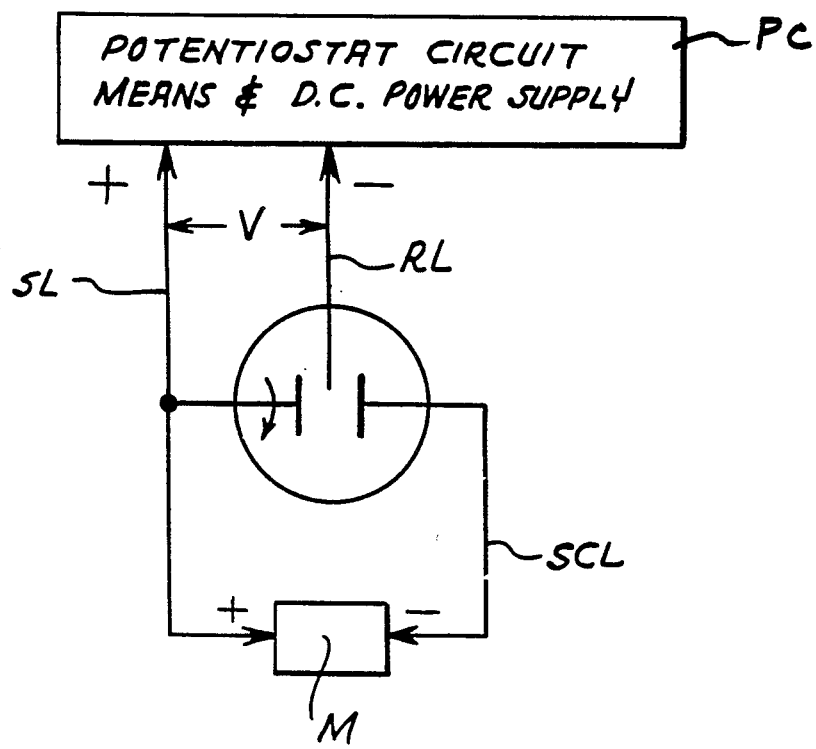
FIG. 1 is a schematic representation of the improved electrolyte element in accordance with the present invention useful in an electrolytic sensing cell or an electrochemical sensing cell and embodying the invention.
FIG. 15 is a schematic representation, in block form, of potentiostatic circuit means and sensing circuit means connected to a three electrode sensor of FIG. 14.

Now referring to the drawings, the electrolyte element EL, FIG. 1, of the present invention will be described in detail in the form it may be used in any electrochemical sensor. The basic material used is a solid, perfluorinated, ion-exchange polymer that has been equilibrated with an acid or a mixture of acids to solvate the hydrogen ions of the sulfonic acid groups of the ion-exchange polymer to provide the hydrogen bonding network in the polymer that maintains the conductivity of the polymer without the addition of water. I have found that the solvation of the hydrogen ions of the polymer can also be achieved by relatively weak acids such as boric acid other than phosphoric acid, by the same process as disclosed for phosphoric acid in the above referenced U.S. Pat. No. 5,164,053, and which disclosure is incorporated herein by reference. In an electrolytic moisture sensor, the conversion of boric acid to anhydrous boric oxide is negligible in comparison to the conversion of phosphoric acid to the anhydrous $P_2O_5$ form under identical operating conditions. Therefore, the resulting boric acid treated polymer membrane EL maintains its ionic conductivity over extended periods of time. The ionic conductivity of the boric acid equilibrated polymer EL is, however, significantly lower compared to the phosphoric acid equilibrated polymer due to the relatively less extensive hydrogen bonding network provided by boric acid compared to phosphoric acid. It has been found that the equilibration of the polymer with boric acid containing a small percentage of phosphoric acid improves the ionic conductivity of the polymer and the conductivity is maintained over extended periods of time, i.e. several months, under very dry environments. The increase in the ionic conductivity of the polymer when equilibrated with a mixture of boric and phosphoric acids is directly related to the concentration of the phosphoric acid in the mixture until all the hydrogen ions of the above mentioned acid groups are solvated by the phosphoric acid. It has therefore been found that depending upon the extent of the ionic conductivity and stability required of a gas sensor in accordance with the gas sensed, the polymer can be equilibrated with boric acid alone or a specific, preselected mixture of boric and phosphoric acids, as illustrated in FIG. 1.

The acid equilibrated, perfluorinated, ion-exchange polymer electrolyte of the "Nafion" type, EL, can be used in any electrolytic cell for any electrolytic reactions where the reactants or the products thereof do not chemically react with the polymer electrolyte, EL, so that the ionic conductivity of the electrolyte is lost, including for the analysis of any gas that can be electrochemically oxidized or reduced. An electrolytic cell may be configured of two or more inert metal or metal alloy electrodes of either the galvanic or polarographic type. Any appropriate electrode material and the voltage of the working or sensing electrode may be selected to drive the desired electrochemical reaction.

An electrolytic cell may be constructed by utilizing the electrolyte element of FIG. 1 in the form of a thin membrane or a thin film. When a thin film is selected, the electrolyte EL may be treated or equilibrated during or after casting a thin film over two or more electrodes on a suitable insulative substrate that is resistant to oxidation and reduction.

When a thin film of the electrolyte El is selected, the preferred mixture for preparing a thin film of the electrolyte EL will now be described. A mixture of 2.5:1:1 of 2.5% of the perfluorinated, ion-exchange polymer, "Nafion", in alcohol, along with 10% phosphoric acid in water with 2.5% boric acid in water. This prepared mixture is used to cast a thin film of a preselected thickness on two or more electrodes arranged on an insulative substrate. This entire assembly, substrate electrodes and prepared mixture, is then heated to above 100 degrees Centigrade to drive off all the solvents until a solid coating EF is formed over the electrodes on the substrate to complete the assembly.

Figure 9:
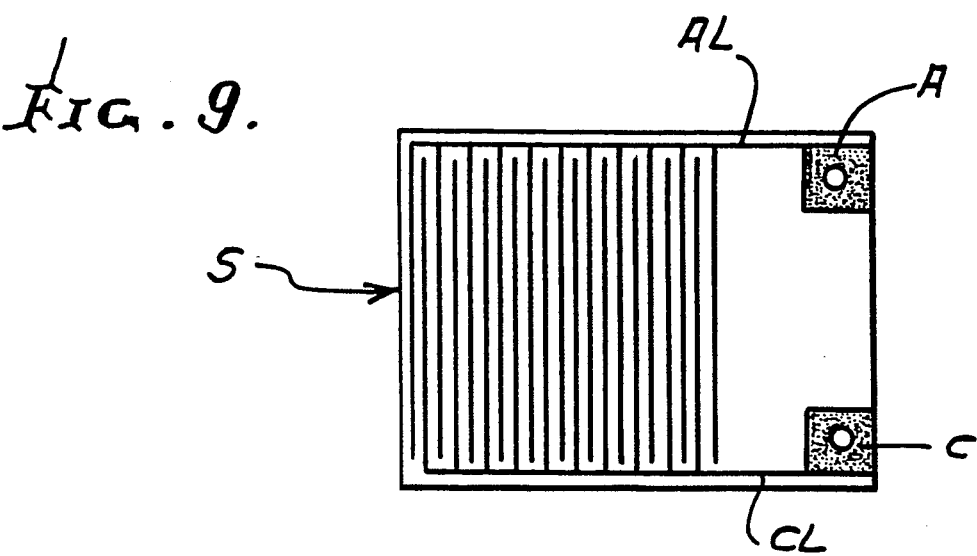
FIG. 9 is a detached, top elevational view of the substrate of FIG. 2 having inter-digital conductive lines deposited thereon for two electrode sensing cell of FIG. 2, without an electrolyte layer thereon.
Figure 10:
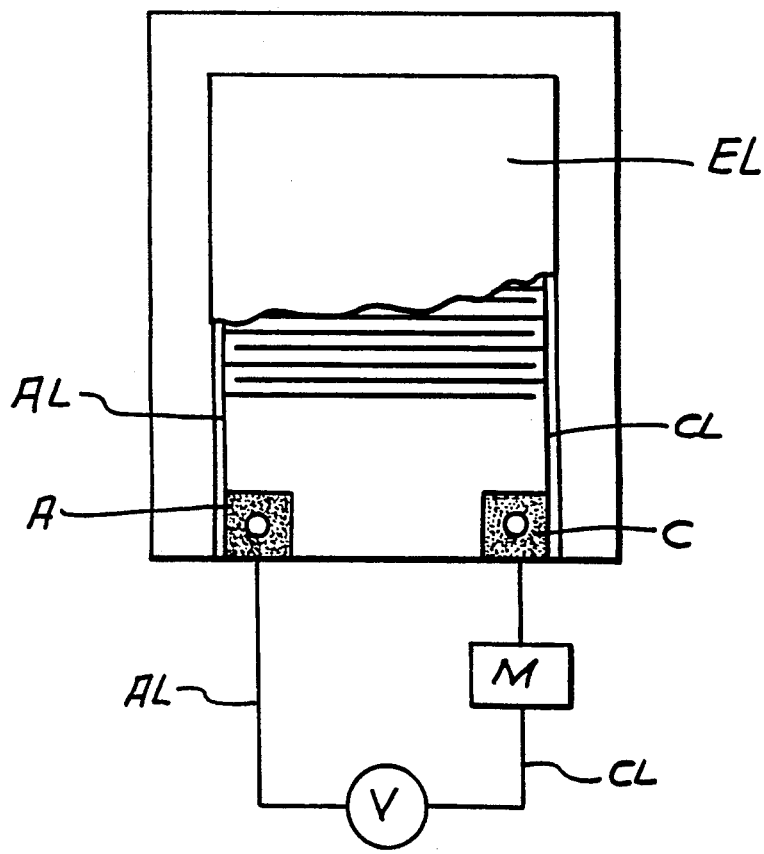
FIG. 10 is a diagrammatic representation of the electrode terminals of FIG. 9 illustrating a voltage potential applied thereto and current sensing circuit.

With the above understanding of the preparation of the electrolyte layer EL in mind, the details of a moisture sensor utilizing the cast electrolyte layer will be examined with respect to FIGS. 2 thru 10. The preferred arrangement of the electrodes is the interdigitated form of electrically conductive lines as best illustrated in FIG. 9, before the electrolyte layer EL is formed thereon. The interdigitated form of conductive lines is well known as is the method of deposition on a suitable substrate. The configuration on a substrate, illustrated in FIG. 9, is for use with a two electrode, electrolytic moisture sensor. The substrate S is constructed of a non-moisture absorbing material such as an alumina and the like. Two electrode terminals for the anode electrode A and the cathode electrode C are defined adjacent one end of the substrate S, the right hand end as illustrated in FIG. 9, to provide good electrical contacts with the conductive lines on the substrate S and to electrically connect to an external lead wire (not shown in FIG. 9). The conductive lines AL are the anode electrode lines that terminate at the anode terminal A and extend across the top face of the substrate in a plurality of parallel conductive lines from one side of the substrate to adjacent the other side thereof as illustrated in FIG. 9.

The anode lines AL are arranged in this fashion in an interdigitated fashion with the cathode lines C1 which terminate at the cathode terminal C as is evident from examining FIG. 9. The cathode lines C1 are arranged in the same parallel arrangement as the anode lines but spaced between the lines AL. The spacing between the lines AL and CL may be any desired spacing in accordance with the operating requirements for the moisture sensor. A typical spacing between the conductive lines AL and CL may be 0.003 inches. It should be understood that the two electrodes are defined by the total length of the lines AL and CL from the terminal portions A and C when the electrolyte EL substantially overlies the lines. In the two electrode configuration, the appropriate voltage, selected in accordance with the desired sensitivity for the electrolytic decomposition of the gas (moisture) being sensed is selected between 10 and 70 volts. This fixed voltage, V, is coupled to the anode and cathode terminals A and C as diagrammatically illustrated in FIG. 10. For constructing a moisture sensor for sensing the moisture in a gas, the electrodes, anode and cathode are constructed of a pure metal or metal alloys from the platinum, Pt, group of metals. With this electrode configuration, then, and the electrolyte EL mixture prepared as described hereinabove is cast over the interdigitated conductive lines AL and CL to form a solid electrolyte coating EL thereover; (see FIG. 2). This electrolytic layer EL when cast over the conductive lines AL and CL cause the conductive lines to be in intimate contact with the electrolytic layer EL deposited thereover. In addition, the electrolyte EL bridges the gap between the lines AC and CL. As is well known, the electrolyte EL constructed of the "Nafion" material is naturally hygroscopic and remains so after being treated with acid, as discussed hereinabove, and therefore absorbs moisture when exposed to a moisture laden gas stream. With the absorption of the moisture by the layer EL and the application of a potential between 10-70 volts across the anode and cathode terminals A and C (see FIG. 9) the gas stream will be electrolytically decomposed. In the case of a moisture laden air stream, the moisture or water, $H_2O$, in the air stream impinging on the electrolyte will cause the water to be split into hydrogen and oxygen. This action causes an electric current to flow between each of the lines AL and CL and thereby to the terminals A and C whereby the magnitude of the current flow is used as a measure of the water or moisture content in the environmental air exposed to the electrolyte EL. It has been found that the use of the electrolyte EL treated with boric acid or a preselected mixture of boric acid and phosphoric acid produces electrolytic gas sensors with greater stability and faster response and recovery times than heretofore thought possible.

Figure 2:
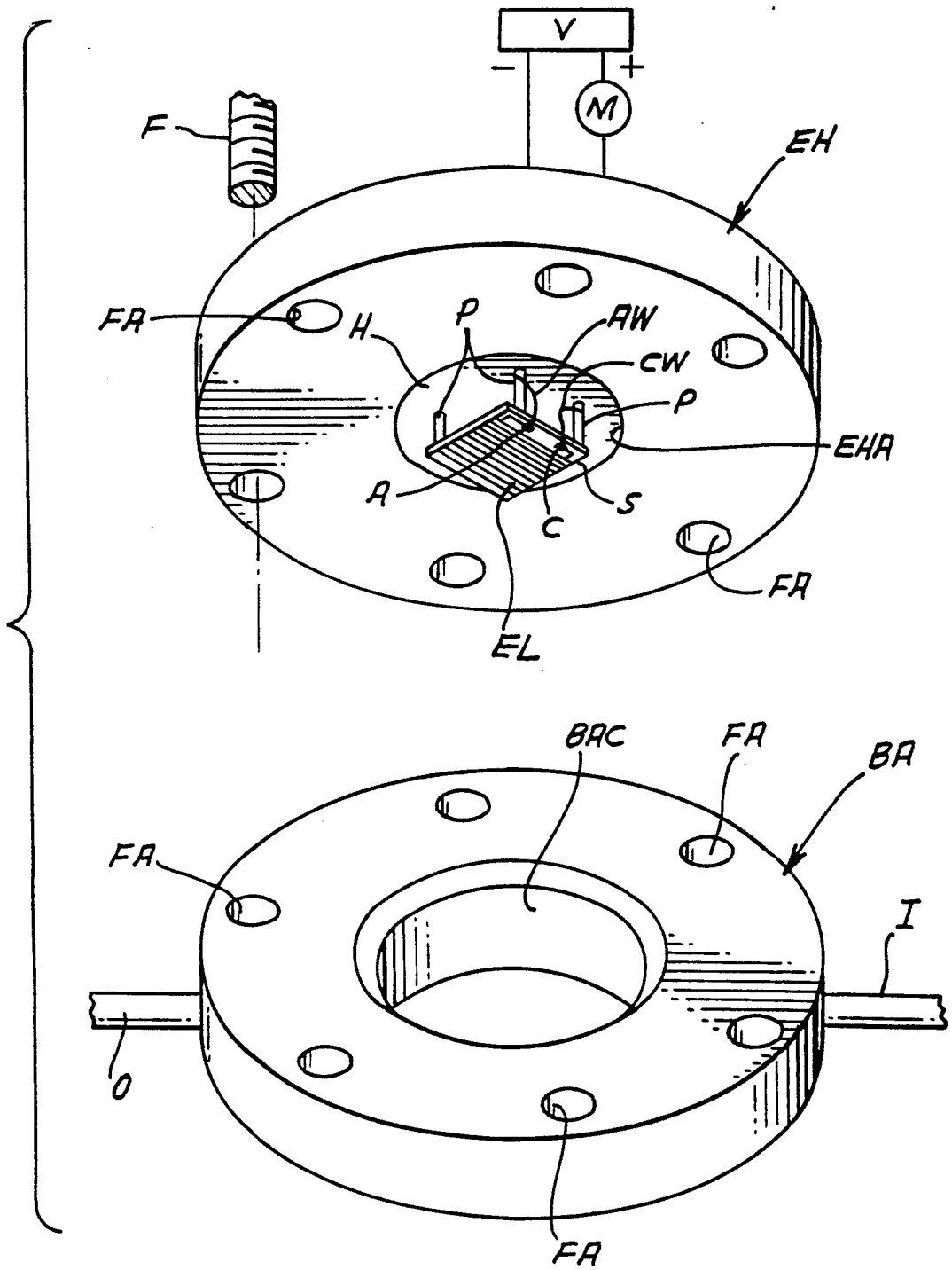
FIG. 2 is an exploded view of an electrolytic moisture sensing cell assembly utilizing the electrolyte element of the type of FIG. 1, with portions broken away and illustrated in block form, and embodying the invention.

Once the substrate S is constructed with the electrolyte film EL overlying the conductive lines AL and Cl (see FIG. 2),the terminals A and C are provided with thin lead wires AW and CW electrically connected to the terminals A and C and extending outwardly therefrom, as illustrated in FIG. 2. The back side of the substrate S is provided with four spaced support posts P secured adjacent to the four corners of the substrate S and extending a preselected distance from the back of the substrate S; see FIG. 2. Three posts P are visible in FIG. 2. The thus defined electrolytic sensor is mounted to a cylindrical electrode holder EH with a central aperture EHA, as can be appreciated from viewing FIGS. 2-5. As seen in FIG. 2, the central aperture EHA has a hermetic compound, non-conductive, cast therein to fill the aperture and hold the substrate S in a spaced relationship with the header H and thereby is supported in a spaced relationship with the back side of the holder plate EH. The thin lead wires AW and CW are electrically connected to a pair of adjacent posts P whereby the posts electrically conduct the currents from the sensor. The posts P extend through the header H and upwardly therefrom on the top side of the holder EH (not shown). This permits access to the conductive posts P for external electrical connections thereto.

The moisture sensor assembly is completed by the provision of block BA for mounting to the holder plate EH. The block BA is also of a cylindrical configuration with a central cavity BAC defined to accommodate the substrate S of FIG. 2 within the cavity BAC; see FIGS. 2, 6-7 for a better appreciation of the details of the block BA. The block BA has a pair of radially extending apertures BAA diametrically arranged on opposite sides of the cavity BAC and defined to communicate with the cavity from the opposite sides of the block BA. The diameters of the apertures BAA are constructed to accommodate and secure gas conveying tubes secured thereto; see FIGS. 6 and 8. The tubes are identified in FIG. 2 as the tube I or gas inlet tubing and the tube O or the gas outlet tubing. As is evident from the drawings, any gas or moisture laden air conveyed into the inlet tubing I will communicate with the cavity BAC and exit the outlet tubing 0. With the assembly of the tubes I and 0 to the apertures BAA for the block BA, the block assembly is completed. The moisture sensor assembly is completed by mounting the holder EH to the top face of the block BA so that the bottom face of the holder plate EH mates with the top face of block BA, (as seen in FIG. 2), the sensor assembly on the substrate S is accommodated within the cavity BAC of the block. This effectively suspends the sensor assembly within the cavity with the electrolyte layer EL in the path of a gas stream conveyed into the inlet I and exit the tube O. This assembly is secured together by means of fasteners F accommodated by the coaxial apertures FA provided around the circumference of the plate EH and block BA, 12 fastener apertures are illustrated. A single fastener F is illustrated with apertures FA for the plate EH and block BA. With the completion of this assembly, the posts P extend outwardly of the header H on the back side, as mentioned hereinabove, so as to be accessible from that side; see FIGS. 4 and 5. With the lead wires AW and CW seen in FIG. 2, the opposite side of the conductive posts P can be connected to a selected, fixed, voltage source V from the back side of the plate EH to the two posts for driving the electrochemical reaction and producing an electrical current flow between the lines AL and CL wherein the magnitude of the current is indicative of the quantity of moisture in the gas fed through the tubing I. The electrical current flow is measured by any suitable sensing circuit, denoted by the block M, for measuring the current flowing in the electrolytic layer EL upon the application of the preselected voltage from the voltage source V thereto. The sensing circuit can be readily calibrated so that the quantity of moisture can be directly read out by any presently known circuit.

Although, the presently preferred embodiment for a two electrode, electrolytic sensor is constructed as described hereinabove and illustrated in FIG. 2, it should be recognized that a sensing cell for producing electrolytic action can be produced in accordance with the teaching's of the present invention by the use of a membrane of the solid, perfluorinated, ion-exchange polymer treated with boric acid or the above described mixture of boric acid and phosphoric acid to function as the electrolytic element EL. In this arrangement the membrane element EL is constructed as disclosed in U.S. Pat. No. 5,164,053 and is used with a pair of gas permeable or diffusion electrodes of the type disclosed in U.S. Pat. No. 5,085,760 referenced hereinabove. Specifically the electrode disclosed in the '760 patent commercially available from the Prototech Company of Newton, Mass. having the desired high surface area metal catalyst diffusion surface, all as specifically disclosed in col. 6 of the '760 patent and which disclosure is incorporated herein by reference. The membrane EL may be sandwiched between the anode and cathode electrodes in the configuration disclosed in U.S. Pat. No. 5,164,053, a galvanic configuration. Alternately, the diffusion electrodes may be on the same side of the membrane EL and in a preselected, spaced relationship thereon to provide the desired electrolytic action. When the membrane EL is utilized, contact rings, such as the rings 15 and 16 are secured to the electrodes with output leads as disclosed and discussed in U.S. Pat. No. 5,164,053.

Figure 11:
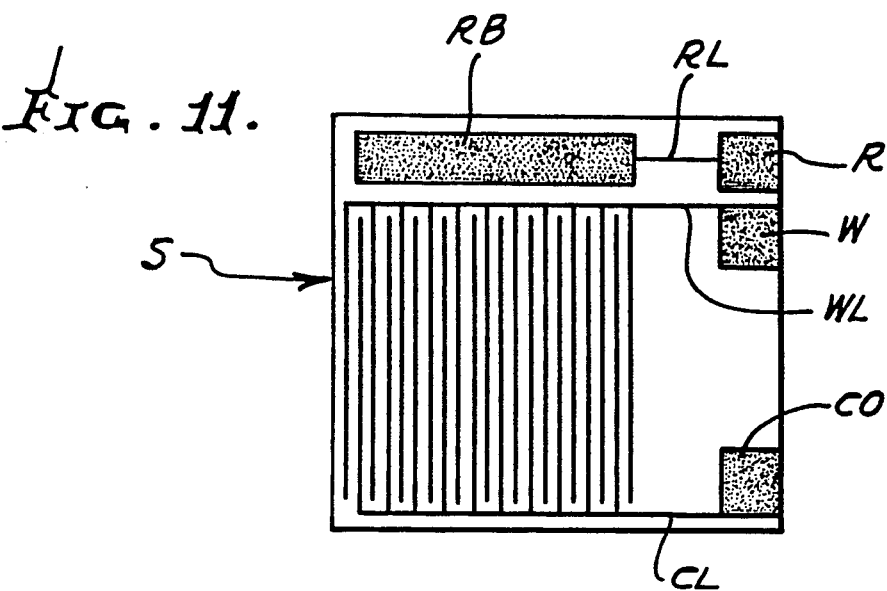
FIG. 11 is a detached, top elevational view of a substrate of the type of FIG. 9 having inter-digitated conductive lines deposited thereon for a 3 electrodes for use in a 3 electrode sensor of the type of FIG. 2.
Figure 12:
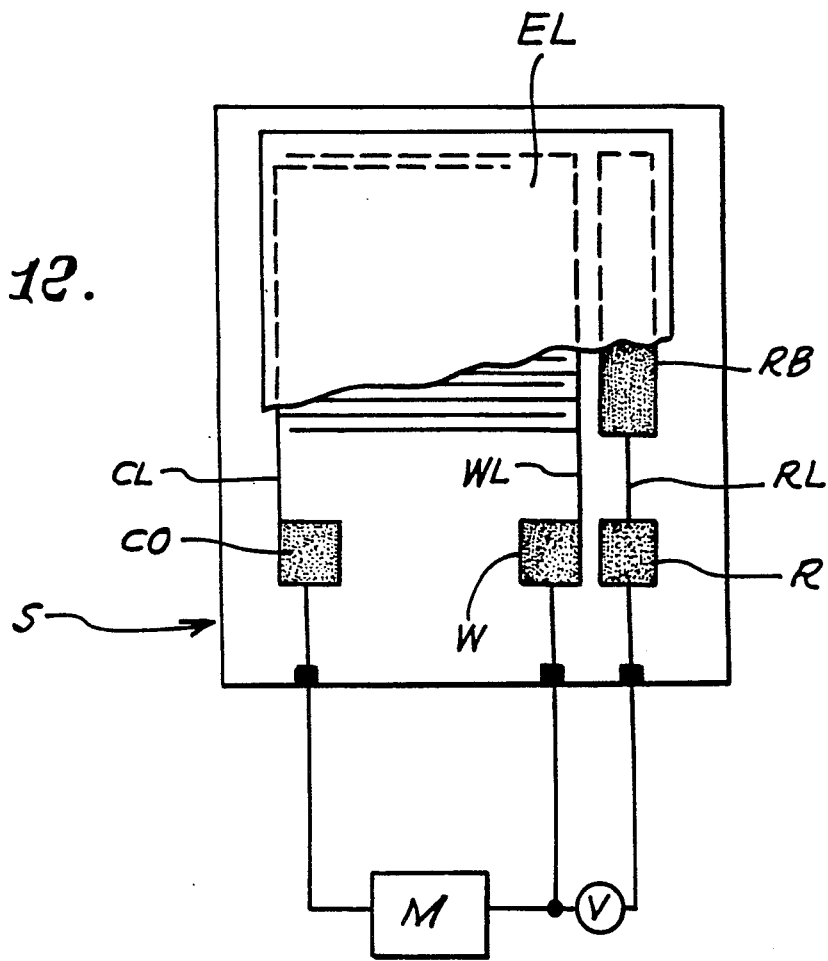
FIG. 12 is a diagrammatic representation of the 3 electrode configuration of the type of FIG. 11 illustrating the connection of a fixed voltage potential between the working and reference electrodes and a sensing circuit in block form connected between the sensing and counter electrodes and embodying the invention.

Now referring to FIG. 11, a three electrode, polarographic type of gas sensor of the type utilizing a thin film of electrolyte EL prepared as discussed hereinabove and deposited on the substrate S with the conductive lines CL and WL as disclosed in conjunction with FIG. 9. The difference is that in FIG. 11, the third or reference electrode R is also deposited on the top surface of the substrate S as illustrated. The two electrodes of FIG. 11 are identified as counter, CO, and working, W, with the connected electrical lines being correspondingly identified as the lines CL and WL. In the same fashion, the terminal portions of the two electrodes on the substrate S are identified as the CO and W terminals and arranged in a spaced relationship on the substrate S adjacent the edge spaced from the lines CL and WL. The reference electrode terminal R is arranged along the same edge as the two electrodes CO and W and arranged in a spaced relationship with the working terminal W. The reference terminal R is connected by means of a conductive line RL to a conductive block RB arranged in a spaced relationship with the conductive lines CL and WL, the block having a preselected width and a length substantially coextensive with the conductive lines as illustrated in FIG. 11. The electrolyte layer EL can then be cast over the conductive lines and block RB as in the previously described embodiment with only the terminal portions CO, W and R being exposed; see FIG. 12. In this three electrode configuration, the metals selected for the electrode are in accordance with the gas to be sensed. When oxygen, hydrogen, hydrogen sulfide and carbon monoxide gases are to be sensed, all the electrodes may be pure metal or a metal alloy catalyst from the platinum group of metals. When sulphur dioxide, nitric oxide and nitrogen dioxide gases are to be sensed, the working and counter electrodes may be of pure gold or a gold alloy catalyst The reference electrode R is provided with a fixed potential with respect to the working electrode W. The voltage to be selected is selected in accordance with the particular metal for the electrode and the selected gas to be sensed. In this embodiment, the electrolytic layer EL is deposited over the conductive lines CL and WL and the reference block RB. In this fashion, then, the gas sensor is "tuned" to a sense a specific one of the aforementioned gases by the selection of the potential selected and applied to the electrode R and between and the other two electrodes.

The voltage selected for application between the reference and working electrodes is maintained at a substantially constant voltage level through the provision of conventional potentiostat circuit means such as diagrammatically illustrated in FIG. 15. Similarly, a suitable sensing circuit coupled between the electrodes W and CO may be utilized to sense the magnitude of the current generated by the electrochemical reaction and is indicated by the blocks M in FIGS. 10 and 12.

Figure 13:
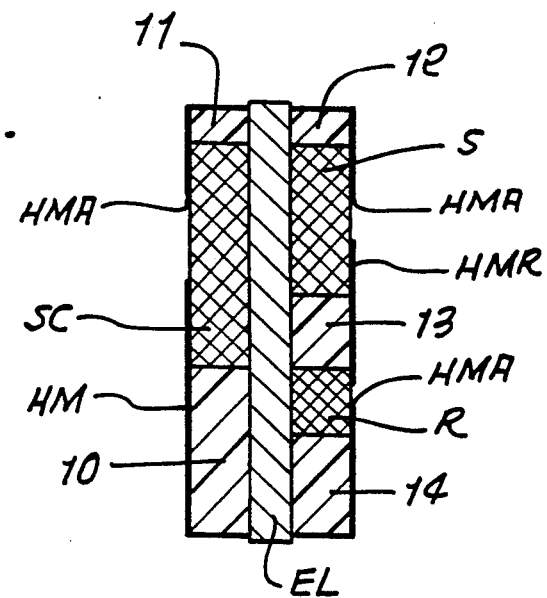
FIG. 13 is a partial, front cross-sectional assembly view of a three electrode, electrochemical sensing cell utilizing the electrolyte of FIG. 1 and embodying the invention.
Figure 14:
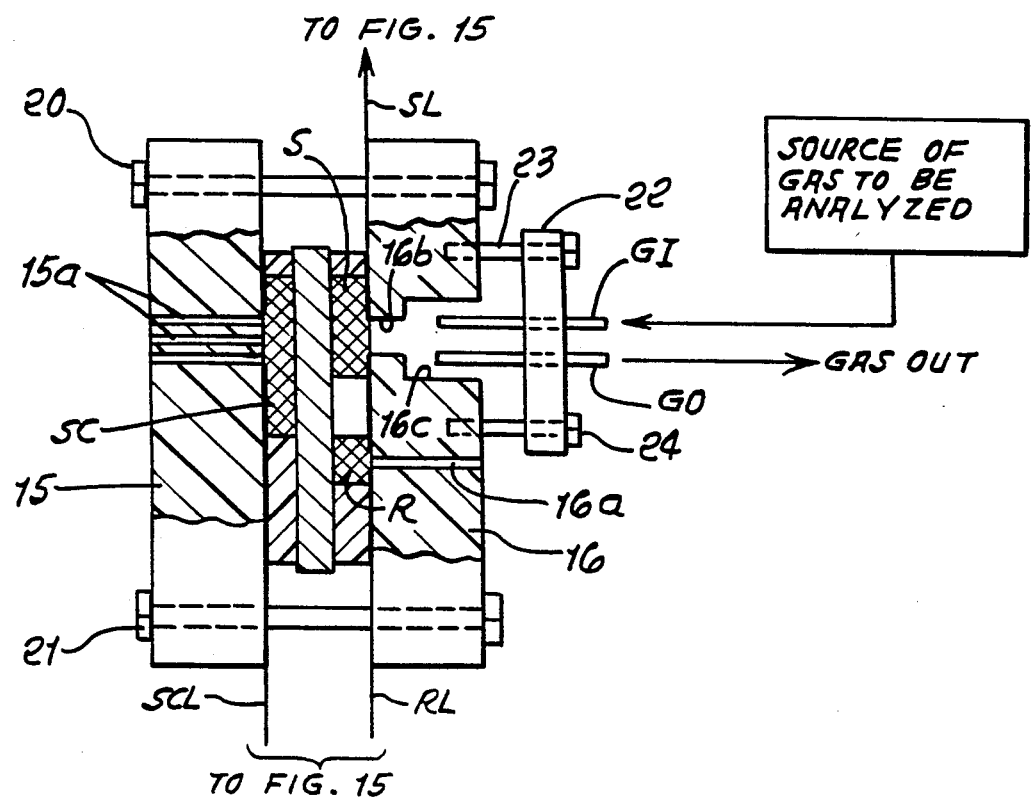
FIG. 14 is a front cross-sectional view, with portions in elevation, of the assembly of the sensor of FIG. 13 for electrochemically sensing of certain gas species.

Now referring to FIGS. 13 and 14, the use of a thin membrane treated with phosphoric acid to maintain its conductivity is illustrated in a three electrode configuration for sensing individual gases. In FIG. 13, the assembly of the sensing cell is illustrated. As illustrated, the three gas diffusing electrodes, S, SC and R, are of the type described hereinabove and as disclosed in U.S. Pat. No. 5,085,760. The sensing gas diffusing electrode S is mounted with one surface integrally in contact with the electrolyte layer EL and which surface mounts the desired catalytic surface with the opposite surface to be exposed to a gas to be analyzed. On the same side of the element EL is mounted the gas diffusing electrode R with its catalyst surface in intimate engagement with the electrolyte membrane EL and the opposite side adapted to be exposed to the environmental air. The third electrode is the secondary gas diffusion electrode SC and is mounted on the opposite side of the element EL from the other two electrodes. The catalytic surface of the electrode SC is in contact with the electrolyte EL and the opposite side is adapted to be exposed to air. As illustrated in FIG. 13, the electrode SC is maintained in the illustrated position by the two insulative spacers 10 and 11 which may be constructed of Teflon. The spacer 10 is arranged below the electrode SC and the element EL while the spacer 11 is arranged above the electrode SC and the element EL. This arrangement of the spacers 10, 11 and electrode SC is maintained by an apertured holding member HM. The aperture HMA is defined to expose the electrode SC to air over a preselected area intermediate its ends as illustrated. The electrodes S and R are arranged with three insulative spacers 12, 13 and 14 on the opposite side of the element EL as illustrated. The spacer 12 is arranged at the top of the electrode S with the spacer 13 arranged below it and in engagement with the electrode R. The spacer 14 fills in the space below the R electrode. This arrangement of the 3 spacers and electrodes S and R is maintained by a holding member HMR having a pair of apertures HMA for exposing the electrodes to air as illustrated. The members HM and HMR have a shallow U-shaped configuration for clamping the electrodes and spacers together in the vertical orientation, illustrated in FIG. 13.

Now referring to FIG. 14, the sensor assembly utilizing the cell of FIG. 13 will be examined. The cell of FIG. 13 has omitted the conductive rings carrying electrical output leads for purposes of explanation. It should be considered that the assembly of FIG. 14 is provided with conductive rings of the type disclosed in U.S. Pat. No. 5,164,053 arranged in contact with the exterior surfaces of the three electrodes and have electrical lead wires electrically connected thereto. The lead wire SL extends from adjacent the conductive ring (not shown) for the electrode S and similarly the leads RL and SCL from adjacent the electrodes R and SC. The cell of FIG. 13 is clamped between a pair of insulative plates 15 and 16 arranged on opposite sides of the cell. The plates 15 and 16 may be constructed of an acrylic material. The plate 15 is provided with a plurality of apertures $15^a$ extending horizontally through the plate to be aligned with the aperture HMA for the holding member HM to thereby expose the electrode SC to air. The plate 16 has an aperture $16^a$ extending vertically therethrough and positioned to be in alignment with the aperture HMA for the frame member HMR and thereby expose the reference electrode R to the environmental air. The gas to be analyzed is conveyed through the aperture $16^b$ for the plate 16 so as to be in alignment with the aperture HMA of member HMR to permit the gas to be analyzed to engage the surface of electrode S. The plates 15 and 16 are maintained in compressive relationship with the sensor by means of a pair of fasteners 20 and 21 extending through the plates adjacent opposite ends thereof, as illustrated in FIG. 14.

The gas to be analyzed is illustrated as being derived from a source illustrated in block form. A pair of gas tubes GI and GO are illustrated supported by a plate 22 which in turn is supported in a spaced relationship with the outside surface of the plate 16. This is realized by the provision of a pair of supporting threaded fasteners 23 and 24 extending adjacent ends of the member 22 and secured to the plate 16 as illustrated. The support member 26 mounts the tubes GI and GO through suitable apertures and have a length to extend adjacent the aperture $16^b$. For this purpose, the plate 16 is provided with an enlarged aperture $16^c$ to accommodate the tubes GI and GO. The tube GI is connected to the source of gas to be analyzed and is thereby conveyed through the tube to be discharged so as to impinge against the electrode S to be sensed. The aperture $16^c$ is provided with a sealed closure (not shown for simplicity purposes) to seal off the open end thereof. The gas then exits the aperture $16^c$ through the tubing GO. The electrodes R and S are coupled by means of the respective lead wires RL and SL to a suitable potentiostat circuit means PC as illustrated in FIG. 15 to provide a constant potential difference between the electrodes in accordance with the gas to be sensed. The gases that may be sensed by this sensor are any gas that can be electrochemically oxidized or reduced. For example, if it is desired to sense oxygen, hydrogen, hydrogen sulfide and carbon monoxide, the three electrodes may be of a pure metal or a metal alloy catalyst from the platinum group of metals with a selection of a suitable voltage between the sensing and reference electrodes. Similarly to sense sulfur dioxide, nitric oxide and nitrogen dioxide, the sensing electrode S and the secondary electrode SC may be constructed of pure gold or a gold alloy catalyst with the application of the appropriate voltages connected to the three electrodes to drive the electrochemical reaction.

The current generated by the electrochemical reaction flows between sensing electrode S and the secondary electrode SC and may be externally sensed, measured and indicated by any conventional sensing circuit for performing these functions. This is illustrated in FIG. 15 by the block M.

It should now be appreciated by those skilled in the art that the present invention teaches the improved treatment of a perfluorinated, ion-exchange polymer with boric acid or a mixture of boric acid and phosphoric acid for use as a sensor electrolyte and which permits construction of gas sensors with greater stability and faster response and recovery times in a relatively inexpensive fashion. The electrolyte may be utilized in either a solid, membrane form or a thin film cast on a substrate.

What is claimed is:

1. An electrolyte for use in a sensing cell for sensing the concentrations of an electrochemically active gas in a gas mixture or for electrolytically decomposing a gas, said electrolyte comprising a solid, perfluorinated, ion-exchange polymer material equilibrated with a preselected mixture of phosphoric and boric acid or solely boric acid in an amount fo maintain the ion conductivity of the polymer whereby sensors utilizing said electrolyte material produces sensing cells of improved ionic conductivity that is maintained over extended periods of time and of greater stability, faster response and recovery times.

2. A method of preparing an electrolytic sensor including the steps of providing an insulative, non-moisture absorbing substrate, mounting a plurality of electrodes to said substrate, preparing a mixture of 2.5:1:1 of 2.5% of an ion-exchange polymer in alcohol along with 10% phosphoric acid in water and 2.5% boric acid in water, casting a thin film of a set thickness of said thus prepared mixture over the electrodes on said substrate, and heating the substrate assembly to above 100 degrees Centigrade to drive off all the solvents until a solid coating of said ion-exchange polymer is formed over said electrodes whereby the resulting electrolyte is maintained ionic conductive at temperatures of up to approximately 180 degrees Centigrade.

3. A method for electrolytically sensing the moisture content in a gas down to sub-parts per billion levels with fast response and recovery time, including the steps of providing a solid, perfluorinated, ion-exchange polymer electrolyte element that has been pre-equilibrated with boric acid or a preselected mixture of boric acid and phosphoric acid so that the electrolyte element is maintained conductive to temperatures up to approximately 180 degrees Centigrade whereby said electrolyte element is useful in an electrolytic cell for any electrolytic reactions where the reactants or the products thereof do not chemically react with the electrolyte element so that the ionic conductivity of the electrolyte element is lost, and attaching a plurality of electrodes to one or both sides of the electrolyte element, and applying an electric potential between said electrodes of a set value for electrolytically decomposing the moisture from any moisture bearing gas exposed to the electrolyte element whereby the external current flow between the electrodes is a measure of the sensed moisture content of said gas.

4. A method for electrolytically sensing the moisture in a gas as defined in claim 3, including the step of selecting a pure metal or metal alloy from the platinum group of metals for the electrodes thereof and providing a voltage between the electrodes set between 10–70 volts.

5. A method of preparing an electrolyte element for a sensor for use in an electrolytic sensor including the steps of providing a thin membrane consisting of a solid, perfluorinated, ion-exchange polymer conductive element to function as an electrolyte element for said sensor, treating said electrolyte element with an acid consisting of boric acid or a set mixture of boric acid and phosphoric acid for maintaining the ionic conductivity of the electrolyte element at temperatures up to approximately 180 degrees Centigrade and thereby maintaining improved ionic conductivity that is maintained over extended periods of time.

6. A method of preparing an electrolyte element in the form of a thin film for use in an electrolytic sensor, including the steps of providing a liquid form of a perfluorinated, ion-exchange polymer in alcohol and mixing with 10% phosphoric acid in water and 2.5% boric acid in water.

7. An electrolytic sensing cell for sensing moisture and the like comprising a solid, perfluorinated, ion-exchange polymer electrolyte element, a non-moisture absorbing substrate means for supporting the electrolyte element and permitting a preselected gas to be electrolized to be exposed to the electrolyte element, said polymer electrolyte element further characterized as having been pre-equilibrated with preselected amounts of boric acid and phosphoric acid for maintaining the ionic conductivity of said electrolyte element at temperatures up to approximately 180 degrees Centigrade and maintaining improved ionic conductivity that is maintained over extended periods of time, and a plurality of electrodes constructed of a preselected metal or metal alloys arranged at spaced locations on said substrate and with said electrolyte element overlying said electrodes, the electrodes being adapted to receive a set electrical potential for driving the electrolysis process of the preselected gas exposed to said electrolyte element.

8. An electrolytic sensing cell as defined in claim 7 wherein said electrodes are selected from the platinum group of metals.

9. An electrolytic sensing cell as defined in claims 7 or 8 wherein said substrate means comprises alumina.

10. A moisture sensor comprising an insulative, non-moisture absorbing substrate, a plurality of electrodes deposited on the substrate and a thin, solid film of a perfluorinated, ion-exchange polymer conductive element deposited over the electrodes to function as the electrolyte for the sensor, said film of ion-exchange polymer conductive element having been pre-equilibrated with a boric acid for maintaining the ionic conductivity of said electrolyte up to temperatures of approximately 180 degrees Centigrade and functioning as the electrolyte moisture sensing element for the sensor to absorb moisture upon the application of a set electrolizing potential between said electrodes.

11. A moisture sensor as defined in claim 10 wherein said electrodes are arranged in an interdigitated grid of a pure metal or metal alloy from the platinum group of metals with an interelectrode spacing of a set distance for measuring moisture in a gas down to the low parts per billion level.

12. A moisture sensor as defined in claim 10 or 11 wherein said polymer conductive element is pre-equilibrated with a set combination of boric and phosphoric acids.

13. A moisture sensor as defined in claim 10 or 11 wherein said substrate comprising alumina.

14. A moisture sensor as defined in claim 10 or 11 wherein the set electrolizing potential is set between 10–70 volts in accordance with the desired sensitivity for the moisture sensor.

15. An electrolytic cell comprising an insulative substrate resistant to oxidation and reduction, a plurality of electrodes mounted on said substrate in a set spaced relationship, and a thin film of a perfluorinated, ion-exchange polymer electrolyte element cast over said electrodes, said thin film having been pre-equilibrated with a boric acid or a set mixture of boric acid and phosphoric acid so that the electrolyte element is maintained conductive to temperatures of approximately 180 degrees Centigrade, said electrodes being adapted to have an electrical potential applied thereto for decomposing a gas exposed to said electrolyte element.

16. An electrolytic cell as defined in claim 15 wherein the plurality of electrodes are arranged in an interdigitated grid of a pure metal or metal alloy from the platinum group of metals.

17. An electrolytic cell as defined in claim 16 wherein the plurality of electrodes are working, counter and reference electrodes.

18. An electrolytic cell as defined in claim 15 wherein the plurality of electrodes comprise a sensing and secondary electrode and a reference electrode arranged on said substrate in a set spaced relationship with the sensing and secondary electrodes, and means for applying a set electrical potential between said sensing and reference electrodes, said electrolyte element being cast over said reference electrode along with said plurality of electrodes.

19. An electrolytic cell as defined in claim 18 wherein all said electrodes of said cell are constructed of a pure metal or metal alloy catalyst from the platinum group of metals for sensing oxygen, hydrogen, hydrogen sulfide and carbon monoxide gases.

20. An electrolytic cell as defined in claim 18 wherein said sensing and secondary electrodes are constructed of pure gold or a gold alloy catalyst for sensing sulphur dioxide, nitric oxide and nitrogen dioxide gases.

21. An electrochemical cell for detecting a gas in the presence of air arranged in a polarographic cell type of configuration for detecting gases that may be electrochemically oxidized or reduced; the cell comprising a solid, perfluorinate, ion-exchange polymer electrolyte element with a sensing gas diffusion electrode, a secondary gas diffusion electrode and a reference gas diffusion electrode attached to said electrolyte element in a preselected geometrical configuration, said solid polymer electrolyte element is further characterized as having been pre-equilibrated with an acid for maintaining the ionic conductivity of said polymer electrolyte element at temperatures up to approximately 180 degrees Centigrade, means for containing and supporting the thus defined polarographic sensing cell elements and for distributing a gas to be detected to the surface of the sensing gas diffusion electrode and adapted for exposing said secondary and reference electrodes to the ambient air to thereby provide an electrical current representative of the quantity of the reactant gas detected by said gas diffusion electrode.

22. An electrochemical cell as defined in claim 21 wherein said acid for pre-equilibrating said polymer comprises phosphoric acid or boric acid—phosphoric acid solution.

23. An electrochemical cell as defined in claim 21 wherein said gas diffusion electrodes are constructed from a pure metal or metal alloy catalyst from the platinum group of metals for sensing oxygen, hydrogen, hydrogen sulfide and carbon monoxide gases.

24. An electrochemical cell as defined in claim 21 wherein said sensing and secondary electrodes are constructed of pure gold or a gold alloy catalyst for sensing sulphur dioxide, nitric oxide and nitrogen dioxide.

25. An electrochemical cell for detecting a gas in the presence of air arranged in a polarographic cell type of configuration for detecting gases that may be electrochemically oxidized or reduced; the cell comprising a solid, perfluorinate, ion-exchange polymer electrolyte element with a sensing gas diffusion electrode, a secondary gas diffusion electrode and a reference gas diffusion electrode attached to said electrolyte element in a set geometrical spaced configuration; said solid polymer electrolyte element is further characterized as having been pre-equilibrated with an acid for maintaining the ionic conductivity of said polymer electrolyte element at temperatures up to approximately 180 degrees Centigrade, means for containing and supporting the thus defined polarographic sensing cell elements and for distributing a gas to be detected to the surface of the sensing gas diffusion electrode and adapted for exposing said secondary and reference electrodes to the ambient air, and potentiostat circuit means are connectable between said sensing electrode and reference electrode for maintaining a set potential on said sensing electrode relative to said reference electrode for driving the electrochemical reaction in accordance with the gas to be detected.

26. An electrochemical cell as defined in claim 25 including circuit means adapted to be connected between said sensing and secondary electrodes for providing an electrical signal representative of the quantity of the sensed gas.

27. An electrochemical cell as defined in claim 25 for sensing oxygen, hydrogen, hydrogen sulfide and carbon monoxide gases wherein said diffusion electrodes are constructed from a pure metal or metal alloy catalyst selected from the platinum group of metals.

28. An electrochemical cell as defined in claim 25 for sensing sulfur dioxide, nitric oxide and nitrogen dioxide gases wherein said sensing and secondary electrodes are constructed with a pure gold or gold alloy catalyst.

* * * * *